(12) United States Patent
Palese (10) Patent No.: US 9,192,371 B2
(45) Date of Patent: Nov. 24, 2015

(54) KNOTLESS SUTURE ANCHOR AND METHOD OF USING SAME

(71) Applicant: Biomet Sports Medicine, LLC, Warsaw, IN (US)

(72) Inventor: Christopher Palese, South Whitley, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 32 days.

(21) Appl. No.: 13/791,072

(22) Filed: Mar. 8, 2013

(65) Prior Publication Data

US 2014/0257355 A1    Sep. 11, 2014

(51) Int. Cl.
*A61B 17/04* (2006.01)

(52) U.S. Cl.
CPC ..... *A61B 17/0401* (2013.01); *A61B 2017/0409* (2013.01); *A61B 2017/0412* (2013.01); *A61B 2017/0422* (2013.01); *A61B 2017/0445* (2013.01); *A61B 2017/0446* (2013.01); *A61B 2017/0458* (2013.01)

(58) Field of Classification Search
USPC .......................................................... 606/232
See application file for complete search history.

(56) References Cited

U.S. PATENT DOCUMENTS

| 5,324,308 | A  | * | 6/1994 | Pierce .......................... 606/232 |
| 5,679,723 | A  | * | 10/1997 | Cooper et al. ................ 523/115 |
| 7,674,276 | B2 | * | 3/2010 | Stone et al. ................... 606/232 |
| 7,713,285 | B1 |   | 5/2010 | Stone et al. |
| 7,976,565 | B1 |   | 7/2011 | Meridew |
| 8,512,405 | B2 |   | 8/2013 | Baird |
| 2006/0235413 | A1 |   | 10/2006 | Denham et al. |
| 2008/0097604 | A1 | * | 4/2008 | Strobel et al. .............. 623/13.14 |
| 2008/0275469 | A1 | * | 11/2008 | Fanton et al. ................. 606/139 |
| 2011/0166599 | A1 | * | 7/2011 | Jervis et al. ................... 606/232 |
| 2014/0257381 | A1 |   | 9/2014 | Palese |

* cited by examiner

*Primary Examiner* — Tuan V Nguyen
(74) *Attorney, Agent, or Firm* — Schwegman Lundberg & Woessner, P.A.

(57) ABSTRACT

A suture anchor including a first portion and a second portion. The first portion defining a first suture bore and having an angled distal surface that extends in a plane oblique to a longitudinal axis of the suture anchor. The second portion defining a second suture bore and having an angled proximal surface that is complementary to the angled distal surface. The angled proximate surface extends in a plane oblique to the longitudinal axis. In a first configuration, the first portion and the second portion are aligned along the longitudinal axis, and the first suture bore is aligned with the second suture bore. In a second configuration, the first portion and the second portion are offset with respect to the longitudinal axis, and the first suture bore is offset from the second suture bore to retain a suture within the first suture bore and the second suture bore.

18 Claims, 5 Drawing Sheets

KNOTLESS SUTURE ANCHOR AND METHOD OF USING SAME

FIELD

The present disclosure relates to a knotless suture anchor and a method of using the knotless suture anchor.

BACKGROUND

This section provides background information related to the present disclosure, which is not necessarily prior art.

Surgeons often use suture anchors to secure bone and tissue in place during a surgical procedure. A suture is connected to the anchor, which is typically implanted in bone. The suture is often connected to the anchor with a knot, which can be difficult to tie and makes tensioning cumbersome, particularly during surgery. The present teachings eliminate the need for connecting the suture to the anchor with a knot by providing a knotless suture anchor and method of using the same.

SUMMARY

This section provides a general summary of the disclosure, and is not a comprehensive disclosure of its full scope or all of its features.

The present teachings provide for a suture anchor including a first portion and a second portion. The first portion defining a first suture bore and having an angled distal surface that extends in a plane oblique to a longitudinal axis of the suture anchor. The second portion defining a second suture bore and having an angled proximal surface that is complementary to the angled distal surface. The angled proximate surface extends in a plane oblique to the longitudinal axis. In a first configuration, the first portion and the second portion are aligned along the longitudinal axis, and the first suture bore is aligned with the second suture bore. In a second configuration, the first portion and the second portion are offset with respect to the longitudinal axis, and the first suture bore is offset from the second suture bore to retain a suture within the first suture bore and the second suture bore.

The present teachings also provide for a system for knotlessly anchoring a suture. The system includes a cannula defining a center bore. A trocar is configured for receipt in the center bore. A deployment shaft is coupled to the cannula. A suture anchor is configured to be mounted to the trocar at a distal end of the cannula. The suture anchor includes a first anchor portion defining a first suture bore, and a second anchor portion defining a second suture bore. Actuation of the deployment shaft draws the second anchor portion against the first anchor portion and proximally toward the distal end of the cannula to misalign the first suture bore and the second suture bore to enable a suture to be secured in the first suture bore and the second suture bore.

The present teachings further provide for a method of knotlessly securing a suture to a suture anchor. The method includes implanting the suture anchor in a bone hole with an insertion tool, the suture anchor including a first portion defining a first suture bore and a second portion defining a second suture bore, the suture extending through the first and the second suture bores. The method further includes moving the second portion of the suture anchor relative to the first portion of the suture anchor using the insertion tool to misalign the first portion and the second portion, and to misalign the first and the second suture bores to retain the suture within the first and the second suture bores.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
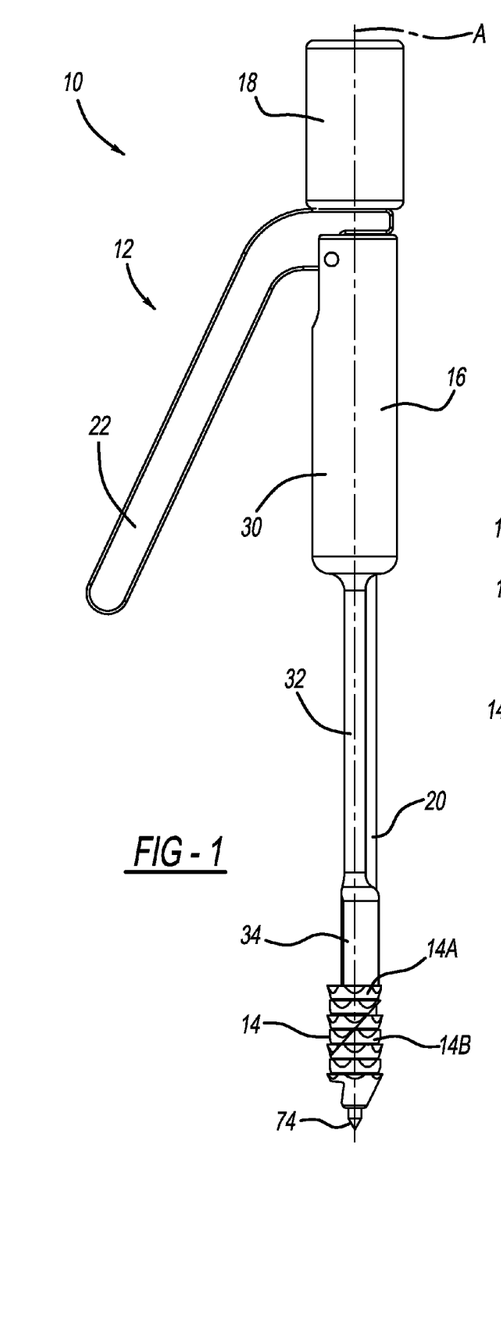
FIG. 1 is a side view of a knotless suture anchor assembly according to the present teachings.
Figure 2:
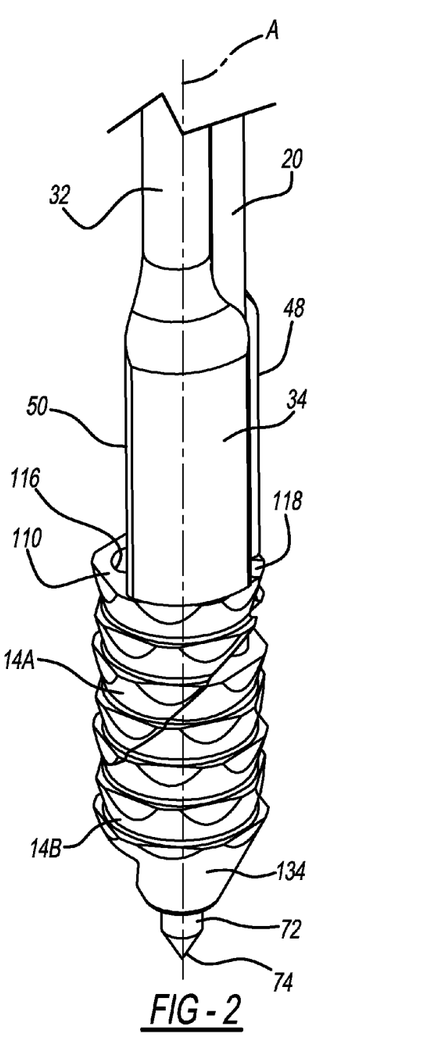
FIG. 2 is a close-up view of a distal portion the knotless suture anchor assembly of FIG. 1.
Figure 3:
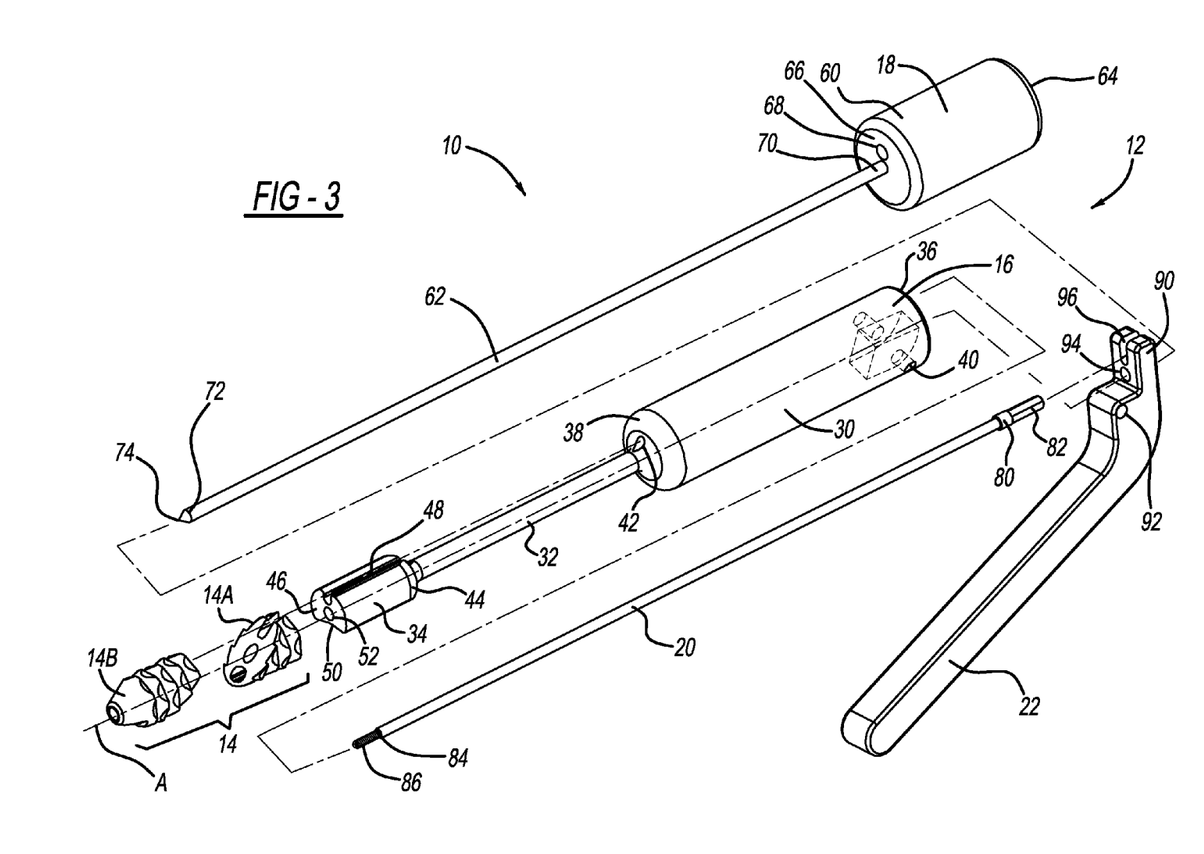
FIG. 3 is an exploded view of the knotless suture anchor assembly of FIG. 1.

With initial reference to FIGS. 1-3, a knotless suture anchor assembly according to the present teachings is generally illustrated at reference numeral 10. The assembly 10 generally includes an insertion tool 12 and a suture anchor 14. The insertion tool 12 includes a cannula 16, a trocar 18, a deployment shaft 20, and a handle 22.

The cannula 16 includes a proximal body 30, an elongated shaft 32, and a distal body 34. The proximal body 30 includes a proximal end 36 that is opposite to a distal end 38. Extending transverse through the proximal body 30 near the proximal end 36 is a bore 40, which is defined by the proximal body 30. The bore 40 extends generally perpendicular to, and offset from, a longitudinal axis A of the knotless suture anchor assembly 10 (FIGS. 1 and 2, for example). The proximal body 30 also defines a longitudinal bore 42 extending through the proximal body 30 between the proximal end 36 and the distal end 38. The longitudinal bore 42 extends generally parallel to, and spaced apart from, the longitudinal axis A.

The elongated shaft 32 extends from the distal end 38 of the proximal body 30 to a proximal end 44 of the distal body 34. The elongated shaft 32 has a diameter that is smaller than a diameter of the proximal body 30 and smaller than a diameter of the distal body 34.

The distal body 34 includes a distal end 46 that is opposite to the proximal end 44. The distal body 34 defines a channel 48 that extends across the distal body 34 generally between the proximal end 44 and the distal end 46. The channel 48 extends generally parallel to, and spaced apart from, the longitudinal axis A (FIGS. 1 and 2, for example).

The distal body 34 further includes a recessed portion 50 at a side of the distal body 34 generally opposite to the channel 48. The recessed portion 50 provides clearance for a suture 150 coupled to the suture anchor 14, as further described herein. The channel 48 provides a clearance for the deployment shaft 20, which extends through the channel 48 as described herein.

The distal end 46 of the distal body 34 is generally planar and extends in a plane that is generally perpendicular to the longitudinal axis A. The suture anchor 14 is arranged at the distal end 46 of the distal body 34 on the trocar 18, as explained further herein. The cannula 16 defines a center bore 52 that extends through the cannula 16 along the longitudinal axis A between the distal end 46 of the distal body 34 and the proximal end 36 of the proximal body 30.

The trocar 18 generally includes a trocar handle 60 and an elongated shaft 62. The trocar handle 60 includes a proximal end 64 and a distal end 66, which is opposite to the proximal end 64. The trocar handle 60 defines a bore 68, which extends between the proximal end 64 and the distal end 66 of the trocar handle 60. The bore 68 need not extend entirely to the proximal end 64, and thus may terminate prior to reaching the proximal end 64 to form a blind bore. The bore 68 is sized and positioned to accommodate the deployment shaft 20 as further described herein.

The elongated shaft 62 includes a proximal end 70 and a distal end 72, which is opposite to the proximal end 70. The proximal end 70 is connected to the distal end 66 of the trocar handle 60. At the distal end 72 of the elongated shaft 62 is a pointed tip 74. The elongated shaft 62 is generally rigid and the pointed tip 74 is configured to permit the trocar 18 to pierce bone and form a bone hole as further described herein.

The deployment shaft 20 includes a proximal end 80 and a coupling member 82 at the proximal end 80. The coupling member 82 can be any suitable coupling member to couple the deployment shaft 20 to the handle 22, such as a surface configured to be rigidly secured in the channel. The deployment shaft 20 further includes a distal end 84, which is opposite to the proximal end 80. At the distal end 84 is a threaded portion 86, which can engage the suture anchor 14 to connect the deployment shaft 20 to the suture anchor 14, as described further herein. The deployment shaft 20 is generally rigid, and can be made of any suitable rigid material, such as a rigid metal or polymer.

The handle 22 includes a flange 90. The flange 90 defines a first bore 92, a second bore 94 orthogonal to the first bore 92, and a channel 96 parallel to the second bore 94. The handle 22 is pivotally coupled to the proximal body 30 with a suitable fastener extending through both the first bore 92 of the flange 90 and the bore 40 of the proximal body 30 of the cannula 16. The handle 22 is arranged such that the second bore 94 is aligned with the center bore 52 of the cannula 16 and the channel 96 is aligned with the longitudinal bore 42 of the cannula 16.

As assembled, the elongated shaft 62 of the trocar 18 extends through both the second bore 94 of the handle 22 and the center bore 52 of the cannula 16. The flange 90 of the handle 22 is between the trocar handle 60 and the proximal end 36 of the cannula 16. Thus, the distal end 66 of the trocar handle 60 is seated on the flange 90 of the handle 22. The distal end 72 of the elongated shaft 62 extends out from within the center bore 52 beyond the distal end 46 of the distal body 34. The suture anchor 14 is seated on the distal end 72 of the elongated shaft 62, and the pointed tip 74 of the elongated shaft 62 extends out from within the suture anchor 14.

The deployment shaft 20 is connected to the handle 22 through cooperation between the coupling member 82 of the deployment shaft 20 and the channel 96 of the flange 90. When the trocar handle 60 is seated on the flange 90 of the handle 22, the bore 68 of the trocar handle 60 accommodates the coupling member 82, which extends beyond the flange 90 of the handle 22. The deployment shaft 20 extends through the longitudinal bore 42 of the cannula 16, and further extends to and through the channel 48 of the distal body 34. The threaded portion 86 at the distal end 84 of the deployment shaft 20 couples with the suture anchor 14 to retain the suture anchor 14 on the distal end 72 of the trocar 18, as further described herein.

With additional reference to FIG. 4, specific features of the suture anchor 14 will now be described. The suture anchor 14 generally includes a first portion 14A and a second portion 14B. The first portion 14A generally includes a proximal surface 110 and a distal surface 112, which is opposite to the proximal surface 110. The proximal surface 110 is generally planar and extends in a plane generally perpendicular to the longitudinal axis A when the suture anchor 14 is seated on the elongated shaft 62 of the trocar 18. The distal surface 112 is angled with respect to the proximal surface 110 and extends in a plane that is angled and not perpendicular to, or oblique to, the longitudinal axis A when the first portion 14A is seated on the trocar 18.

The first portion 14A defines a center bore 114, a suture bore 116, and a deployment shaft recess or bore 118. The center bore 114 extends between the proximal surface 110 and the distal surface 112 along the longitudinal axis A when the first portion 14A is coupled to the trocar 18. The suture bore 116 also extends between the proximal surface 110 and the distal surface 112. When the first portion 14A is seated on the trocar 18, the suture bore 116 is aligned with the recessed portion 50 of the distal body 34 of the cannula 16, as illustrated in FIG. 3. The suture bore 116 is thus arranged such that it extends generally parallel to a longitudinal axis A and spaced apart from the longitudinal axis A. The deployment shaft recess 118 can be a cutout in the first portion 14A as illustrated, or a bore extending through the first portion 14A. The deployment shaft recess 118 extends between the proximal surface 110 and the distal surface 112. The deployment shaft recess 118 is configured to receive the distal end 84 of the deployment shaft 20. When the first portion 14A is coupled to the cannula 16, the first portion 14A is arranged such that the deployment shaft recess 118 is aligned with the channel 48 of the distal body 34. The deployment shaft recess 118 extends generally parallel to and spaced apart from the longitudinal axis A. The center bore 114 is thus arranged between the suture bore 116 and the deployment shaft recess 118, and is configured to receive the elongated shaft 62 of the trocar 18.

Extending from a periphery of the first portion 14A between the proximal surface 110 and the distal surface 112 are a plurality of retention ribs 120. The retention ribs 120 are generally circular and extend generally radially from the first portion 14A. Also extending from the periphery of the first portion 14A are a plurality of retention teeth 122. The retention teeth 122 are generally spaced apart along the retention ribs 120. The retention ribs 120 and the retention teeth 122 are configured to engage an inner wall of a bone hole to retain the first portion 14A within the bone hole as further described herein. The retention ribs 120 and the retention teeth 122 can be any suitable retention members suitable for retaining the first portion 14A within a bone hole.

Figures 4, 5:
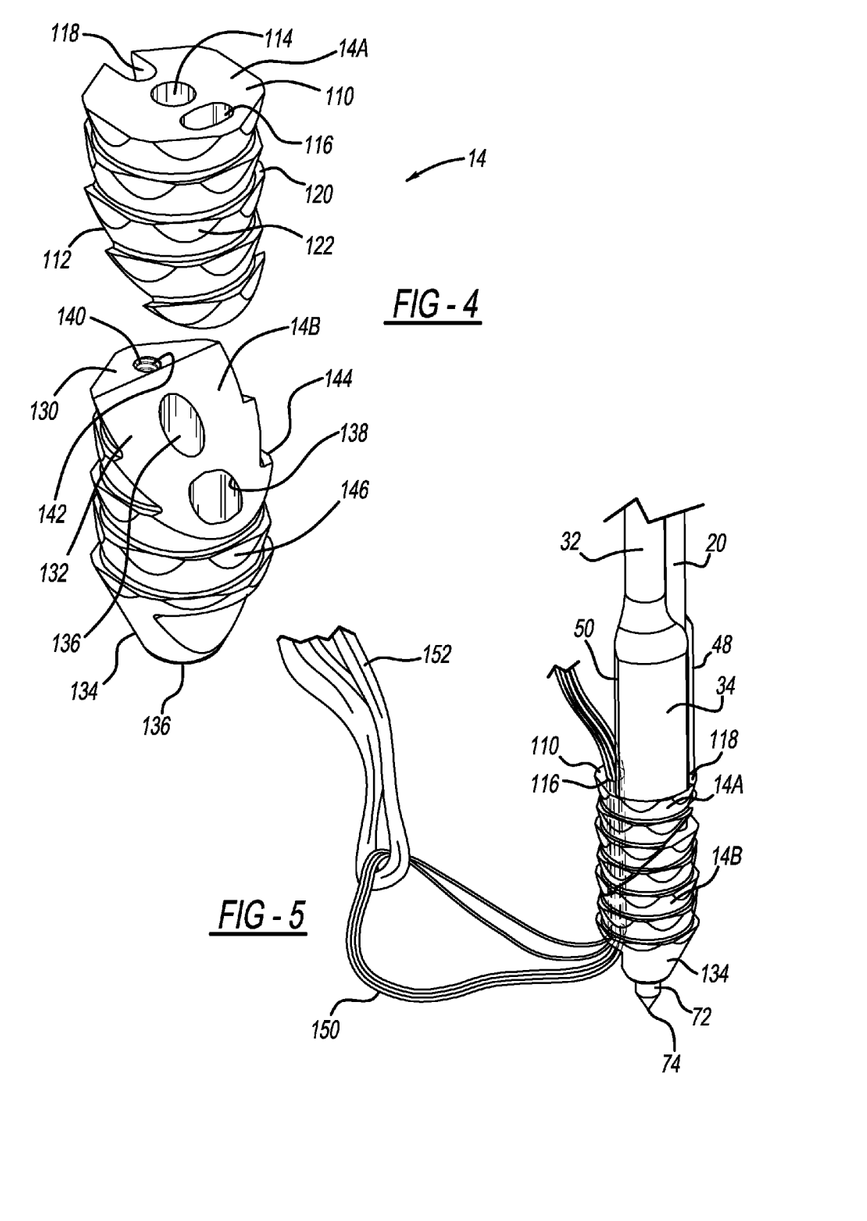
FIG. 4 illustrates a suture anchor according to the present teachings.
FIG. 5 illustrates a suture coupled to both the suture anchor and tissue.

With continued reference to FIG. 4, the second portion 14B of the suture anchor 14 generally includes a first proximal surface 130, a second proximal surface 132, and a distal cone-shaped surface 134. The first proximal surface 130 is adjacent to the second proximal surface 132. The first proximal surface 130 is generally planar and extends in a plane that is generally perpendicular to the longitudinal axis A when the second portion 14B is seated on the trocar 18. The second proximal surface 132 is angled with respect to the first proximal surface 130. The second proximal surface 132 thus extends in a plane that is not perpendicular to, or oblique to, the longitudinal axis A when the second portion 14B is seated on the trocar 18.

The second portion 14B defines a center bore 136, a suture bore 138, and a deployment shaft bore 140. The center bore 136 extends between the second proximal surface 132 and the distal cone-shaped surface 134. The center bore 136 extends along the longitudinal axis A when the second portion 14B is seated on the trocar 18, and thus the center bore 136 of the second portion 14B is aligned with a center bore 114 of the first portion 14A. The longitudinal axis A is also a longitudinal axis of the suture anchor 14. A suture bore 138 extends from the second proximal surface 132 to the distal cone-shaped surface 134. The suture bore 138 extends generally parallel to the longitudinal axis A, but spaced apart therefrom, when the second portion 14B is seated on the trocar 18. The suture bore 138 of the second portion 14B is aligned with the suture bore 116 of the first portion 14A prior to deployment of the suture anchor 14, as described in further detail herein.

The deployment shaft bore 140 extends from the first proximal surface 130 towards the distal cone-shaped surface 134. The deployment shaft bore 140 may extend to the distal cone-shaped surface 134, or may terminate prior to reaching the distal cone-shaped surface 134. The deployment shaft bore 140 may define threads 142 therein. The threads 142 extend from the first proximal surface 130 to any suitable distance within the deployment shaft bore 140 to permit coupling with the threaded portion 86 of the deployment shaft 20. Extending from an outer diameter of the second portion 14B are a plurality of annular retention ribs 144 and a plurality of retention teeth 146. The retention ribs 144 are generally similar to the retention ribs 120 of the first portion 14A, and the retention teeth 146 are generally similar to the retention teeth 122 of the first portion 14A. The suture anchor 14 can be made of any suitable biocompatible material. For example, the suture anchor 14 can be made of a suitable polymer, such as PEEK, or a suitable metallic.

Coupling of the suture anchor 14 with the insertion tool 12 will now be described in additional detail. The first portion 14A of the suture anchor 14 is arranged such that the proximal surface 110 abuts the distal end 46 of the distal body 34, which is part of the cannula 16. The center bore 114 is aligned with the center bore 52 of the cannula 16 and the distal end 72 of the trocar 18 extends through the center bore 114. The deployment shaft recess 118 is aligned with the channel 48 of the cannula 16, and the suture bore 116 is aligned with the recessed portion 50 of the cannula 16.

The second portion 14B of the suture anchor 14 abuts the first portion 14A. Specifically, the second proximal surface 132 of the second portion 14B abuts the distal surface 112 of the first portion 14A. The distal end 72 of the trocar 18 extends through the center bore 136 of the second portion 14B, which is aligned with the center bore 114 of the first portion 14A. The suture bore 138 of the second portion 14B is aligned with the suture bore 116 of the first portion 14A. The deployment shaft bore 140 is aligned with the deployment shaft recess 118 of the first portion 14A.

The deployment shaft 20 extends through the deployment shaft recess 118 of the first portion 14A, and into the deployment shaft bore 140 of the second portion 14B. The threaded portion 86 of the deployment shaft 20 threadably engages the threads 142 of the deployment shaft bore 140 to retain the second portion 14B on the trocar 18. The first portion 14A is thus retained between the second portion 14B and the cannula 16. Although the deployment shaft 20 is illustrated as being retained within the deployment shaft bore 140 with a threaded coupling, the deployment shaft 20 may be retained within the deployment shaft bore 140 in any suitable manner using any suitable coupling, such as a press fit or an overmold.

With additional reference to FIGS. 5-7, a method of using the knotless suture anchor assembly 10 to anchor suture 150 in bone 210 will now be described. Although the suture 150 is described as securing tissue 152 to bone 210, the suture 150 can be used to secure any suitable tissue or bone at any suitable location. The suture 150 can be coupled to the tissue 152 prior to or after the suture anchor 14 is implanted in the bone 210. Prior to implanting the suture anchor 14 in the bone 210, the suture 150 is passed through the suture bore 116 and the suture bore 138 of the suture anchor 14. The suture anchor 14 is then implanted in the bone 210 using the insertion tool 12.

Figure 6:
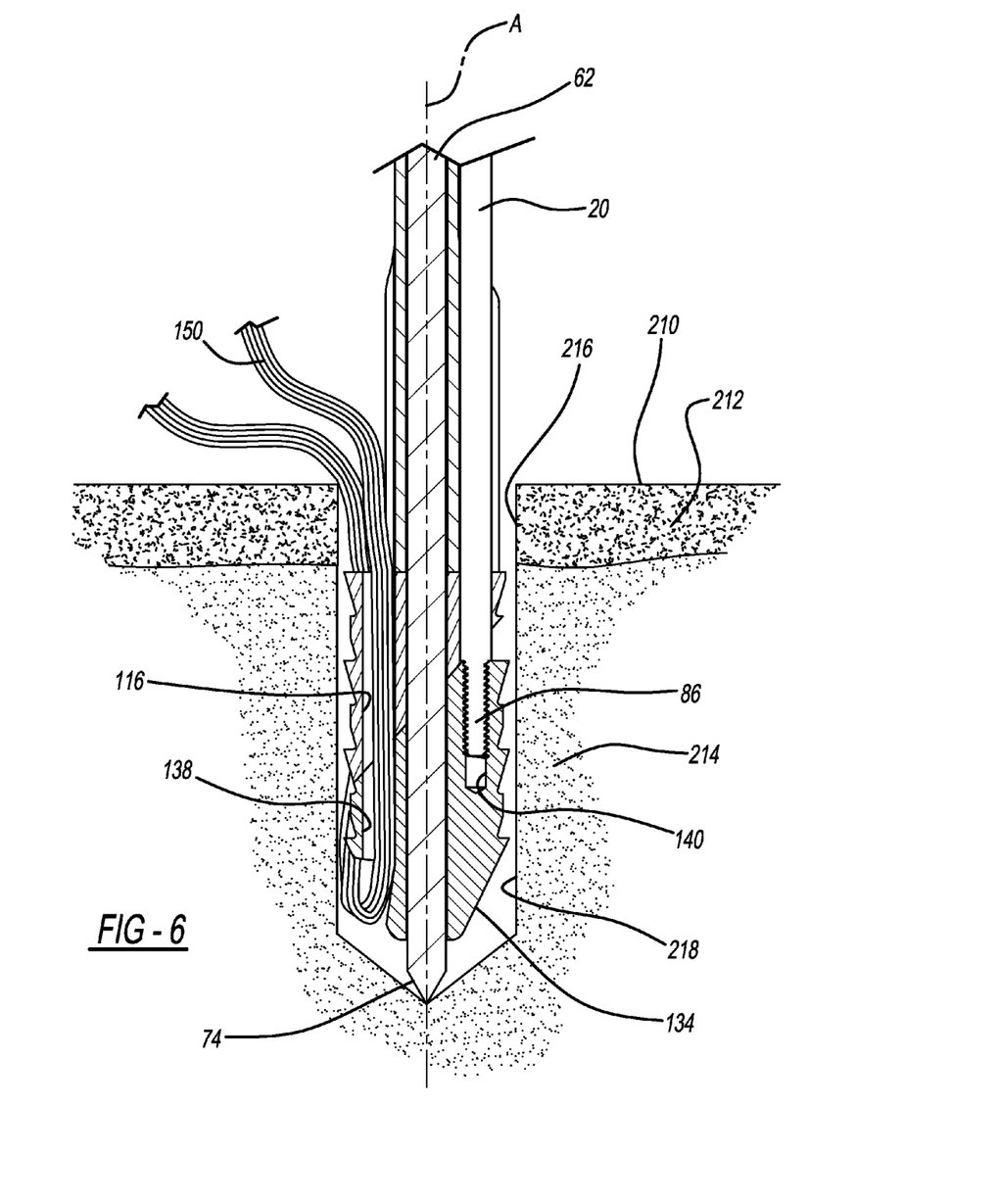
FIG. 6 illustrates the suture anchor with a suture coupled thereto arranged in a bone hole prior to deployment of the suture anchor.

As illustrated in FIG. 6 for example, the suture anchor 14 is implanted in a bone hole 216 extending through cortical bone 212 and into cancellous bone 214. The bone hole 216 may be pre-formed with a suitable drill or punch for example, or the insertion tool 12 may be impacted into the bone 210 to form the bone hole 216. For example, the insertion tool 12 may be arranged such that the pointed tip 74 is at the surface of the cortical bone 212 and then the proximal end 64 of the trocar handle 60 may be impacted, such as with a suitable impactor, in order to drive the suture anchor 14 into the bone 210 and form the bone hole 216.

Figure 7:
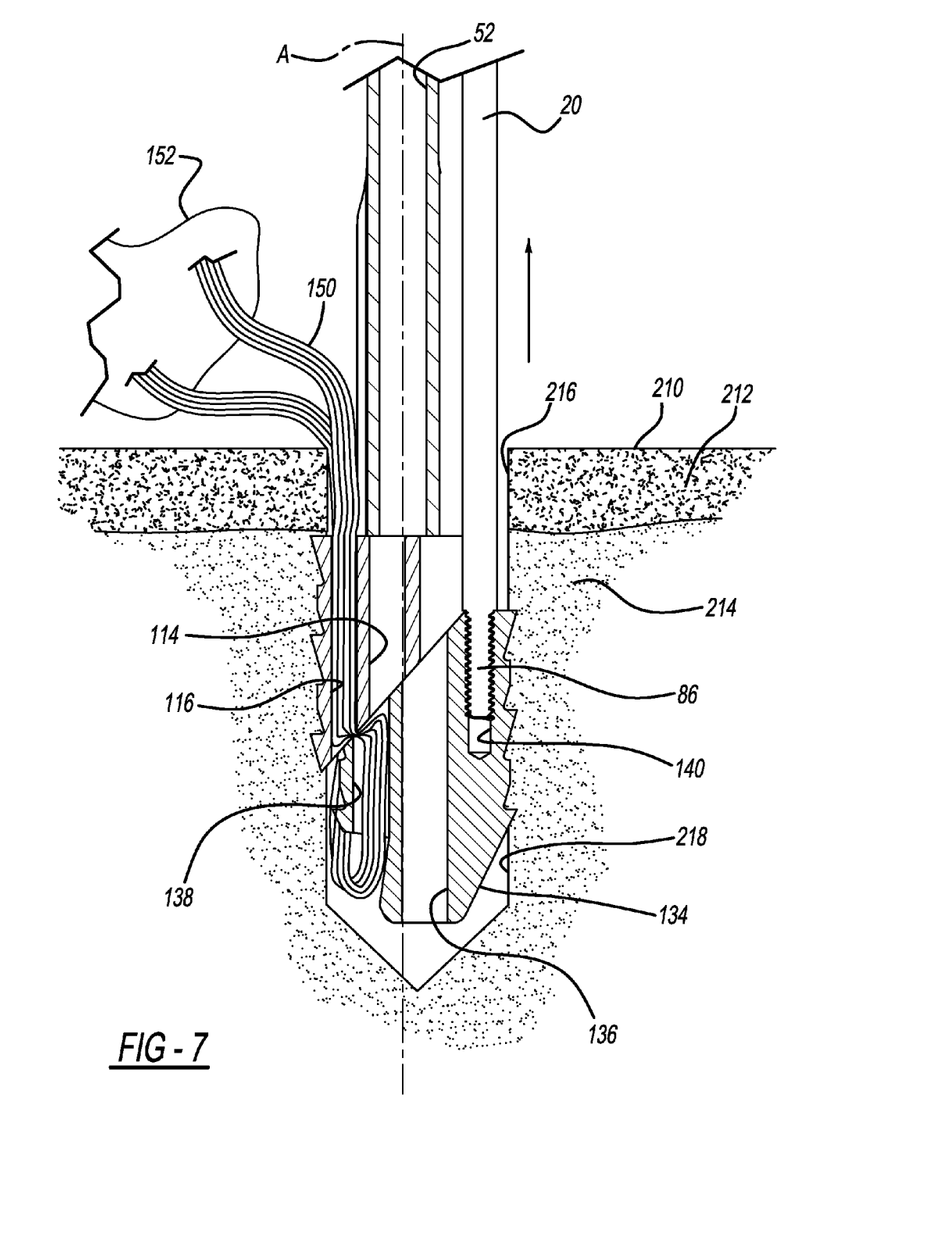
FIG. 7 illustrates the suture anchor deployed in the bone hole to secure the suture to the suture anchor and retain tissue against bone.

With additional reference to FIG. 7, after the suture anchor 14 is seated in the bone hole 216, the trocar 18 is removed from cooperation with the remainder of the insertion tool 12. To deploy the suture anchor 14 and thus retain the suture anchor 14 within the bone hole 216, the handle 22 is depressed, which pulls the distal end 84 of the deployment shaft 20 proximally toward and into the distal body 34 of the cannula 16. Because the deployment shaft 20 is coupled to the second portion 14B of the suture anchor 14, the deployment shaft 20 will pull the second portion 14B proximally toward the cannula 16 and press the second proximal surface 132 of the second portion 14B against the distal surface 112 of the first portion 14A. This movement will force each of the first portion 14A and the second portion 14B radially away from the longitudinal axis A in opposite directions and into engagement with the bone 214 of the inner wall 218 defining the bone hole 216. This movement will also misalign the center bore 114 and the center bore 136 of the first portion 14A and the second portion 14B respectively.

The suture bore 116 and the suture bore 138 of the first portion 14A and the second portion 14B respectively will also become misaligned, which will pinch the suture 150 between the suture bore 116 and the suture bore 138, and thus retain the suture 150 within the suture bores 116 and 138. In this manner, the suture 150 will be coupled to the suture anchor 14 without the need for a knot. Continued actuation of the handle 22 will cause the threaded portion 86 of the deployment shaft 20 to disengage the threads 142 of the deployment shaft bore 140, such as by stripping or pulling out through the threads 142. This continued actuation of the handle 22 will further force the first and second portions 14A and 14B of the suture anchor 14 away from the longitudinal axis A and into the inner wall 218 of the bone hole 216, thereby retaining the suture anchor 14 within the bone hole 216. The tissue 152 coupled to the suture 150 will thus be retained against the bone 210 with the anchored suture 150.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of knotlessly securing a suture to a suture anchor comprising:
   implanting the suture anchor in a bone hole with an insertion tool, the suture anchor including a first portion defining a first suture bore and a second portion defining a second suture bore, the suture extending through the first and the second suture bores;
   moving the second portion of the suture anchor relative to the first portion of the suture anchor using the insertion tool to misalign the first portion and the second portion, and to misalign the first and the second suture bores to pinch the suture between the first and second portions to retain and restrict movement of the suture within the first and the second suture bores along a longitudinal axis of the suture anchor; and
   actuating a deployment shaft of the insertion tool to move the second portion of the suture anchor toward a distal end of a cannula to which the suture anchor is mounted.

2. The method of claim 1, further comprising connecting the suture to a tissue before or after implanting the suture anchor in bone.

3. The method of claim 1, further comprising pressing a handle of the insertion tool to actuate the deployment shaft.

4. The method of claim 1, further comprising removing a trocar to which the suture anchor is seated on from cooperation from the cannula, the suture anchor is arranged at a distal end of the cannula when implanted.

5. The method of claim 1, further comprising tensioning the suture and a tissue coupled thereto prior to moving the second portion of the suture anchor relative to the first portion of the suture anchor.

6. The method of claim 1, further comprising forcing the first portion of the suture anchor and the second portion of the suture anchor into engagement with an inner wall of the bone hole by pulling the second portion of the suture anchor against the first portion of the suture anchor.

7. The method of claim 1, further comprising moving a second angled surface of the second portion of the suture anchor relative to a first angled surface of the first portion of the suture anchor using the deployment shaft to misalign the first and the second suture bores to retain the suture within the first and the second suture bores.

8. A method of knotlessly securing a suture to a suture anchor comprising:
   implanting the suture anchor, the suture anchor including a first portion defining a first suture bore and a second portion defining a second suture bore, the suture extending through the first and second suture bores; and
   moving the second portion of the suture anchor relative to the first portion of the suture anchor to misalign the first and second suture bores to retain and restrict movement of the suture relative to a longitudinal axis of the suture anchor by pinching the suture between the first and the second suture bores, wherein moving the second portion of the suture anchor relative to the first portion of the suture anchor further includes moving the first portion and the second portion of the suture anchor radially away from a longitudinal axis of the suture anchor and in opposite directions.

9. The method of claim 8, wherein implanting the suture anchor includes moving the suture anchor along a first axial direction and wherein moving the second portion of the suture anchor relative to the first portion of the suture anchor includes moving the second portion in a second axial direction opposite the first axial direction.

10. The method of claim 8, wherein implanting the suture anchor includes implanting the suture anchor into a hole formed into bone to retain the suture relative to the bone.

11. The method of claim 8, wherein retaining the suture relative to the suture anchor includes pinching the suture between the first and second suture bores of the suture anchor upon misaligning the first and second portions of the suture anchor.

12. The method of claim 8, further comprising misaligning the first and second suture bores by moving a first angled face of the second portion of the suture anchor relative to a second angled face of the first portion of the suture anchor.

13. The method of claim 8, wherein implanting the suture anchor further includes implanting the suture anchor with an insertion tool axially aligned with the suture anchor and wherein moving the second portion of the suture anchor relative to the first portion of the suture anchor includes axially misaligning the suture anchor relative to the insertion tool.

14. A method of knotlessly securing a suture to a suture anchor comprising:
   positioning a suture anchor having a first longitudinal axis with an insertion tool having a second longitudinal axis while the first and second longitudinal axes are aligned; and
   moving a first portion of the suture anchor relative to a second portion of the suture anchor with the insertion tool to misalign the first and second longitudinal axes and misalign a first suture bore defined by the first portion and a second suture bore defined by the second portion to retain the suture to the suture anchor within the first portion and the second portion relative to the first longitudinal axis without knots by pinching the suture between the first suture bore and the second suture bore.

15. The method of claim 14, wherein moving the first portion of the suture anchor relative to the second portion of the suture anchor includes moving the first portion and the second portion radially away from the second longitudinal axis of the insertion tool.

16. The method of claim 15, wherein positioning the suture anchor further includes positioning the suture anchor into a bone hole in bone and wherein moving the first portion of the suture anchor relative to the second portion of the suture anchor includes moving the first and second portions radially away from the second longitudinal axis in opposite directions and into engagement with the bone of an inner wall defining the bone hole.

17. The method of claim 14, further comprising removing a trochar that extends through a bore in the insertion tool along the second longitudinal axis and through a bore in the suture anchor along the first longitudinal axis to allow the first and second portions of the suture anchor to move.

18. The method of claim 17, further comprising moving a deployment shaft of the insertion tool that is coupled to the second portion of the suture anchor to misalign a first bore in the first portion of the suture anchor with a second bore in the second portion of the suture anchor and pinch the suture within the first and second bores.

* * * * *